United States Patent
Cook

(10) Patent No.: US 6,322,539 B1
(45) Date of Patent: Nov. 27, 2001

(54) IV GUARD

(75) Inventor: Daniel G. Cook, Maple Plain, MN (US)

(73) Assignee: Health & Technology, Inc., Plymouth, MN (US)

( * ) Notice: Subject to any disclaimer, the term of this patent is extended or adjusted under 35 U.S.C. 154(b) by 0 days.

(21) Appl. No.: 09/382,531

(22) Filed: Aug. 25, 1999

(51) Int. Cl.[7] ............................................ A61M 5/32
(52) U.S. Cl. ................................. 604/174; 604/180
(58) Field of Search ........................... 248/102, 104, 248/105, 106; 340/586; 606/234, 235, 236; 215/11.1, 11.3, 11.4, 11.5, 11.6; 604/174

(56) References Cited

U.S. PATENT DOCUMENTS

| | | | |
|---|---|---|---|
| 3,722,508 | 3/1973 | Roberts | 128/133 |
| 3,901,226 | 8/1975 | Scardenzan | 128/133 |
| 4,277,910 * | 7/1981 | Kramer | 215/11 |
| 4,295,293 * | 10/1981 | Baclit | 248/104 |
| 4,320,883 * | 3/1982 | Bass | 248/104 |
| 4,453,933 | 6/1984 | Speaker | 604/179 |
| 4,517,971 | 5/1985 | Sorbonne | 128/133 |
| 4,631,058 | 12/1986 | Raines | 604/263 |
| 4,679,553 | 7/1987 | Proulx et al. | 128/133 |
| 4,898,587 | 2/1990 | Mera | 604/174 |
| 4,919,654 | 4/1990 | Kalt | 604/180 |
| 4,976,698 | 12/1990 | Stokley | 604/174 |
| 5,018,534 | 5/1991 | Grant | 128/877 |
| 5,037,397 * | 8/1991 | Kalt et al. | 604/174 |
| 5,083,732 * | 1/1992 | Akamine | 248/104 |
| 5,116,324 | 5/1992 | Brierley et al. | 604/180 |
| 5,167,240 | 12/1992 | Rozier et al. | 128/888 |
| 5,336,204 | 8/1994 | Matyas | 604/263 |
| 5,344,406 | 9/1994 | Spooner | 604/179 |
| 5,413,120 | 5/1995 | Grant | 128/877 |
| 5,707,348 | 1/1998 | Krough | 602/41 |
| 5,795,335 | 8/1998 | Zinreich | 604/174 |
| 5,885,254 | 3/1999 | Matyas | 604/180 |
| 5,916,199 | 6/1999 | Miles | 604/174 |
| 5,988,752 | 11/1999 | Richards | 297/393 |
| 6,050,976 * | 4/2000 | Thorne et al. | 604/164 |
| 6,119,850 * | 9/2000 | Chen et al. | 206/0.5 |

* cited by examiner

Primary Examiner—Manuel Mendez
(74) Attorney, Agent, or Firm—Kinney & Lange, P.A.

(57) ABSTRACT

An IV guard having a cover with an open back for use in conjunction with an intravenous connection comprising a cannula that is inserted into a vein of an individual. The cannula being inserted through an insertion point in the individual's skin. The cover having an inner hollow cavity defined by a top, a front, and pair of sidewalls that together create a shape of an animal. The open back of the cover allows examination of the cannula and the insertion point which are contained in the inner hollow cavity when the cover is in place over the insertion point.

20 Claims, 2 Drawing Sheets

IV GUARD

BACKGROUND OF THE INVENTION

The present invention relates to protecting an insertion point of either an intravenous (IV) infusion or injection. More particularly, the invention pertains to an IV guard.

IV's have become a widely used and standard technique to introduce a substance into a vein of an individual. The substance can be introduced rapidly by an intravenous injection, or slowly by an intravenous infusion. IV's are typically used to introduce or administer blood or plasma during a blood transfusion; a mixture of glucose (sugar) and saline (salt) or other varied or concentrated nutrients for artificial feeding or hydration; and various drugs or medicines to treat pain, illness or disease.

IV's are typically comprised of a bag or bottle, a tube and a cannula. The bag or bottle store and contain the substance that is to be administered to the individual and is suspended from a holder above the insertion point of the IV. The tube is generally made of clear plastic for easy examination. The tube is connected at one end to the bag or bottle suspended from the holder. The opposite end of the tube is connected to the cannula. The cannula is inserted into the vein of the individual through the skin at the insertion point. After the cannula is inserted into the vein and connected to the tube, it is generally secured in place by surgical tape to the skin surrounding the insertion point. The cannula is secured in place to prevent damage which could otherwise result from its movement relative to the vein or insertion point through the skin.

IV's work well for adults and older children who can understand and appreciate the purpose of the IV and who can comprehend the significance of not disrupting the IV once it is in place. On the other hand, young children are not familiar with and do not understand the importance of an IV. They also can not comprehend for any length of time that they should leave the IV alone. Rather, young children tend to either fear the IV and want it out or are curious of the IV and want to play with it.

Children's fear of the IV arises not only from the pain associated with the cannula being inserted through their skin and into their vein, but also from the presence of the IV after it is inserted. The pain from the insertion or the mere presence of the IV can create extreme anxiety in the child causing them to become scared of the IV and want it removed. The child may also become curious of the tubes, rather than anxious or scared, and try to remove or play with the IV. Movement of the cannula inserted into the individual's arm can result in serious damage to the vein or surrounding tissue, such as being torn or punctured. The cannula can also break apart either partially or completely with a portion partially exposed or completely lodged underneath the surface of the skin. There is no known device that protects the insertion point of an IV while either helping to calm the child's fear or redirect the child's curiosity of the IV.

BRIEF SUMMARY OF THE INVENTION

An IV guard comprising an open-backed cover having an inner hollow cavity that includes a top, a front, and a pair of side walls. The top, front and pair of side walls are connected together to create a shape of an animal. An open bottom of the cover is set upon an area of skin so that the cover surrounds and contains an insertion point of an IV. The IV exits out of the hollow cavity through the open-back of the cover.

DETAILED DESCRIPTION

Figure 1:
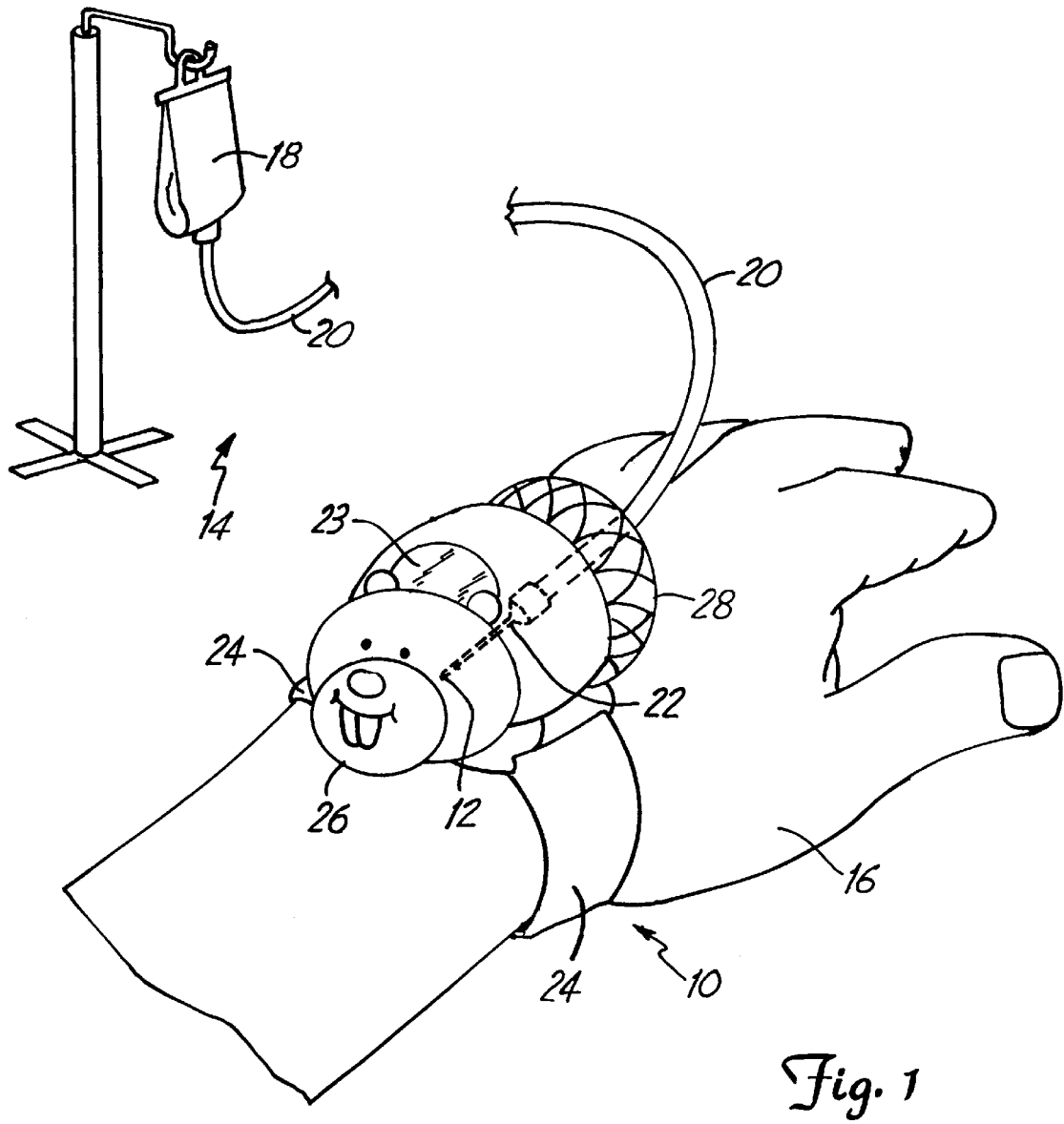
FIG. 1 is a perspective view of the invention placed on a child's arm over an insertion point of an IV.

FIG. 1 is a perspective view of a preferred embodiment of an IV guard 10. The IV guard 10 is placed over an insertion point 12 of either an intravenous infusion or injection 14, more commonly referred to as an IV 14. IV's are typically inserted in a hand or forearm area of an arm 16. IV's 14 are typically comprised of a bag or bottle 18 which contains a substance that is generally inserted or injected into a vein of an individual. A tube 20 connects the bag 18 to a cannula 22 that is inserted through the individual's skin and into the vein. The cannula 22 is shown in phantom in FIG. 1 beneath the IV guard 10. Placing the bag 18 above the point of entry of the cannula 22 in the skin will force the solution out of the bag 18, through the tube 20 and the cannula 22, and into the vein of the individual by gravity. FIG. 1 provides a simplified view of the IV 14 for general reference and orientation. IV's 14 also typically include valve(s) for controlling the flow of fluid into the vein and ports for injecting fluids, such as medication, into the tube 20. IV's 14 can also include an IV controller or IV pump that controls the flow of fluid from the bag or bottle 18 to the cannula 22. IV's 14 can be used for blood transfusions, artificial feeding, rehydration, or administering drugs or medications.

The use of IV's 14 has become standard practice in the medical field. They are very effective for use with adults and older children. Younger children, however, have a difficult time not moving or pulling on the tube 20 of the IV 14 due to either fear or curiosity. The child's handling of the IV 14 can result in pulling the cannula 22 out of the vein or skin causing damage to the vein or surrounding tissue. The cannula 22 can also be bent or can break off causing further injury and requiring additional medical attention.

IV's 14 are typically inserted into the arm 16 on the outside or back of the hand, wrist or forearm area. As illustrated in FIG. 1, the IV guard 10 is placed over an insertion point 12 of the IV 14 through the skin. The IV guard 10 is formed in the shape of an animal, such as a beaver as illustrated in FIG. 1. The IV guard 10 is placed on the arm 16, or over the insertion point 12 so that it faces the individual or child when they look in the general area of the IV 14 or the insertion point 12. The IV guard 10 is preferably colored or painted with characteristics to match the shape of the animal it is formed in. The IV guard 10 is preferably made from polyvinyl chloride and formed by injection molding. Placing the IV guard 10 over the insertion point 12 of the IV 14 directs the individual's or child's attention toward a cute, friendly and familiar animal or object, rather than the unfamiliar IV 14.

The IV guard 10 also preferably includes a window 23. The window 23 allows medical personnel to directly view and examine the cannula 22 and the insertion point 12 that are covered by the IV guard 10. The window 23 is preferably a flat piece of plastic to avoid a distorted view of the area of interest. The window 23 fits into a cut out section of the IV guard 10. The window 23 has a generally oval shape due to the sliced or cut out section of the IV guard 10, which has a curved contour, and the flat surface of the window 23. The window 23 is preferably approximately 18.0 millimeters wide and 13.0 millimeters long.

In a preferred embodiment, the IV guard 10 also includes a pair of adhesive strips 24 which extend from the IV guard 10 to secure it over the insertion point 12. The adhesive strips 24 are preferably non-latex and made of polyvinyl chloride foam or polyester foam. They also have an adhesive placed on an underside that is covered by a tear away strip that is removed prior to use. The adhesive strips 24 are approximately 35.0 to 50.0 millimeters long and 22.0 millimeters wide. Notations can also be made on a top surface of the adhesive strip 24 to indicate when the IV 14 was first inserted, last checked, or other related information. Medical personnel thus have a readily available record of information pertaining to the IV 14. Alternative materials could also be used to construct the adhesive strips 24 provided they are safe to use on the surface of the skin, such as skin safe adhesives and strips that are produced by 3M Medical Specialties.

The IV guard 10 preferably has a front 26 and a back 28. The IV guard 10 is placed over the top of the insertion point 12 of the IV 14 so that the front 26 is seen by the individual or child when they look in the vicinity of the insertion point 12 of the IV 14. The back 28 of the IV guard 10 is at least partially open to allow the tube 20 of the IV 14 to exit from under the IV guard 10. The IV guard 10 is positioned so that the window 23 is directly over the insertion point 12 and cannula 22 to allow for their examination therethrough.

Figure 2:
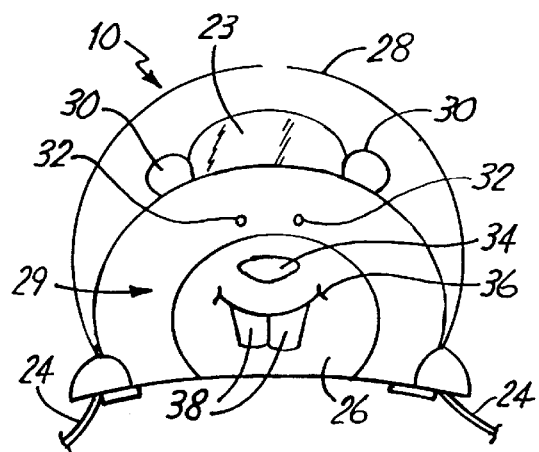
FIG. 2 is a front view of the invention.

FIG. 2 is a front view of the IV guard 10 illustrating what the individual or child would see when they look in the direction or vicinity of the insertion point 12 of the IV 14. The front 26 of the IV guard 10 preferably includes facial features of the animal on a head 29, such as a pair of ears 30, a set of eyes 32, a nose 34 and a mouth 36. A pair of teeth 38 are also preferably included to fit the beaver design of the IV guard 10 as illustrated in FIGS. 1–5. The facial features are preferably created with a warm and friendly appearance to assure the individual or child and help calm any fear or anxiety they may experience. The facial features of the beaver, or any other animal, are preferably shown smiling to appear friendly. Placing the facial features of the animal at the front 26 will direct the child's attention to the IV guard 10, rather than the IV 14.

Focusing the child's attention on the IV guard 10 will make it less likely that the individual or child will notice or pay attention to the IV 14. The individual or child will instead play with or pet their new animal friend rather than pull out the IV 14.

Figure 3:
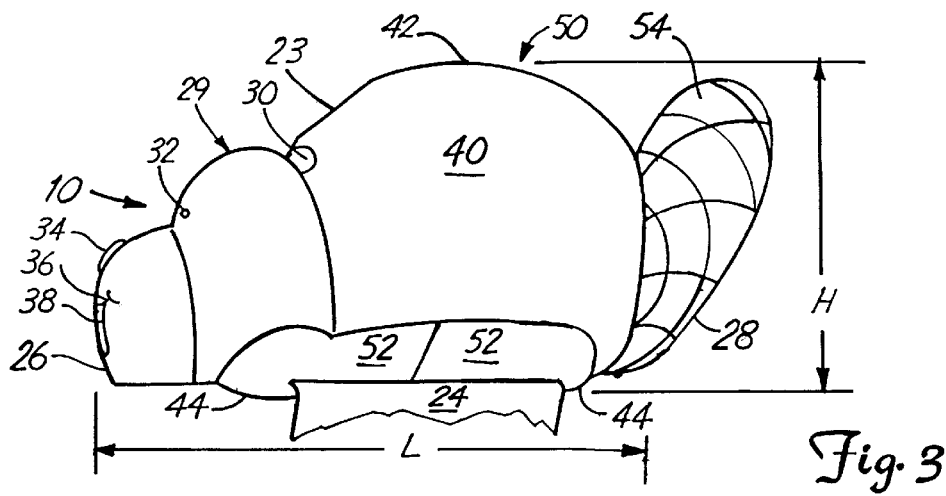
FIG. 3 is a side view of the invention.

FIG. 3 is a side view of the IV guard 10. As illustrated in FIG. 3, the IV guard 10 is further constructed from a pair of sidewalls 40, a top 42, and a bottom 44. The sidewalls 40 are preferably symmetrical about a center line through the IV guard 10 from the front 26 to the back 28. The sidewalls 40 preferably run from the front 26 to the back 28 and from the bottom 44 to the top 42. In a preferred embodiment, a length L of the sidewalls 40 along the bottom 44 (or a length of the IV guard 10 at the bottom 44) is approximately 51.0 millimeters. The sidewalls 40 of the IV guard 10 preferably have a height H of approximately 33.0 millimeters. The length L and height H of the sidewalls 40 should be large enough to ensure that the insertion point 12 and the cannula 22 fit under the IV guard 10.

The shape of the IV guard 10 preferably further includes all of the characteristics of the animal the IV guard 10 is shaped in. The IV guard 10 thus includes a body 50, a set of legs 52 and a tail 54. Other characteristics may also be included depending on what animal the IV guard 10 is shaped in. The IV guard 10 can also be painted in alternative colors than are typical for the shape of the animal.

A portion of the window 23 is also shown cut out of the body 50 behind the head 29 of the IV guard 10. FIG. 3 illustrates the curved nature of the body 50 where the window 23 has been cut in resulting in the generally oval shape of the window 23. The window 23 allows direct viewing from above the IV guard 10 of the insertion point 12 of the IV 14 and the cannula 22. The height H of the IV guard 10, or the sidewalls 40, is also preferably large enough to allow medical personnel to view the cannula 22 and the insertion point 12 of the IV 14 through the open back 28 of the IV guard 10.

Figure 4:
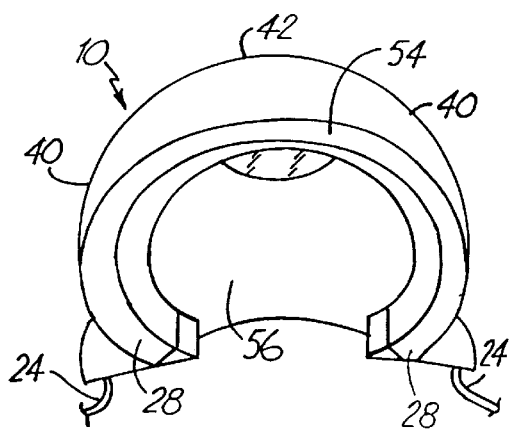
FIG. 4 is a back view of the invention.

FIG. 4 is a back view of the IV guard 10. As illustrated in FIG. 4, the back 28 of the IV guard 10 is open. This allows the tube 20 of the IV 14 to exit out from under the IV guard 10. As illustrated in FIG. 4, the IV guard 10 has an open cavity 56 that is created by the pair of sidewalls 40, the top 42, and the front 26. The cavity 56 is sufficiently large to surround the insertion point 12 and cannula 22 of the IV 14. The tube 20, which is connected to the cannula 22, exits the cavity 56 out of the open back 28 of the IV guard 10. The back 28 of the IV guard 10 is preferably completely open to allow easier access and visual inspection of the insertion point 12 and the cannula 22.

Figure 5:
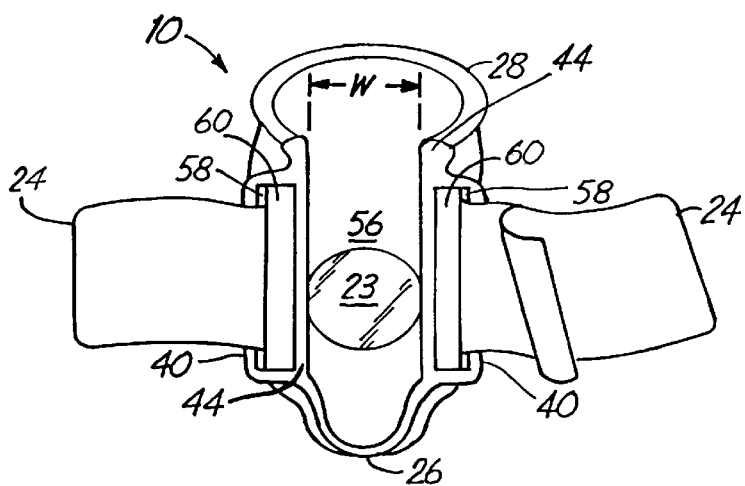
FIG. 5 is a bottom view of the invention.

FIG. 5 is a bottom view of the IV guard 10. As illustrated in FIG. 5, the bottom 44 of the IV guard 10 is preferably open to allow for placement of the IV guard 10 on the surface of the individual's skin to cover the insertion point 12 of the IV 14. The bottom 44 of the IV guard 10 is preferably U-shaped and includes a pair of slots 58 that run along the pair of sidewalls 40. The slots 58 provide a means for mounting a pair of anchors 60 that are secured to and attach the adhesive strips 24 along the side of the IV guard 10. The anchors 60 can either be permanently or replaceably secured in the slots 58. One of the tear away strips placed over the adhesive on the underside of the adhesive strips 24 is shown partially peeled back in FIG. 5. The bottom 44 of the IV guard 10 preferably has a width W of approximately 22.2 millimeters to ensure that the insertion point 12 and the cannula 22 of the IV 14 can be contained within the IV guard 10.

Although the present invention has been described with reference to preferred embodiments, workers skilled in the art will recognize that changes may be made in form and detail without departing from the spirit and scope of the invention. For instance, the IV guard can be shaped in the form of different animals or include different features. The IV guard can also be made out of a different material or secured over the insertion point by other means such as surgical tape. The IV guard provides protection to the insertion point of an IV while helping to calm the child's fear and redirect the child's curiosity of the IV.

What is claimed is:
1. An IV guard for use in conjunction with an intravenous connection having a cannula that is inserted into a vein of an individual through an insertion point in the individual's skin, the IV guard comprising:
 a cover having an inner hollow cavity that includes a top, a front and a pair of sidewalls that together create a shape of an animal in a substantially horizontal position so that the cover protects an intravenous connection having a cannula that is inserted into a vein of an individual through an insertion point in the individual's skin;

a front region located at the front of the cover having a shape of a head and having facial features of an animal, the front region positioned toward the individual when the cover is in place over the insertion point;

a middle region adjoining the front region and having a shape of a body of an animal that includes a set of legs; and a rear region adjoining the middle region at an end opposite the front region and having a shape of a tail of an animal, the rear region being open to allow examination of the cannula and the insertion point which are contained in the inner hollow cavity when the cover is in place over the insertion point.

2. The IV guard of claim 1, wherein the IV guard further includes an adhesive strip secured to the cover to secure the cover to the individual's skin with the insertion point and cannula contained within the inner hollow cavity.

3. The IV guard of claim 2, wherein the adhesive strips are replaceably secured in a slot along a bottom of the sidewalls.

4. The IV guard of claim 2, wherein the adhesive strips are made of polyvinyl chloride foam.

5. The IV guard of claim 1, wherein the cover is made of polyvinyl chloride.

6. The IV guard of claim 1, wherein the cover is approximately 33.0 millimeters high, 51.0 millimeters long and an open bottom of the cover is approximately 22.2 millimeters wide.

7. The IV guard of claim 1, wherein the cover has a shape of a beaver.

8. The IV guard of claim 1, wherein a window is placed along a portion of the top of the cover to allow examination of the cannula and the insertion point.

9. The IV guard of claim 8, wherein the window has an oval shape and is made of a flat piece of plastic.

10. An IV guard for protecting an insertion point of a cannula to an intravenous connection, the IV guard comprising:

a cover having a top, a bottom, a front, a back and a pair of sidewalls to create an inner hollow cavity and an outer appearance of an animal in a substantially horizontal position, wherein the bottom and the back are open so that the cover protects an intravenous connection having a cannula that is inserted into a vein of an individual through an insertion point in the individual's skin;

a front region located at the front of the cover having a shape of a head and having facial features of an animal, the front region positioned toward the individual when the cover is in place over the insertion point;

a middle region adjoining the front region and having a shape of a body of an animal that includes a set of legs;

a rear region adjoining the middle region at the back of the cover and having a shape of a tail of an animal; and an adhesive strip secured to the cover to retain the open bottom of the cover over the insertion point of the cannula.

11. The IV guard of claim 10, wherein a window is placed along a portion of the top of the cover to allow examination of the cannula and the insertion point.

12. The IV guard of claim 11, wherein the window has an oval shape and is made of a flat piece of plastic.

13. The IV guard of claim 10, wherein the cover is made of a polyvinyl chloride.

14. The IV guard of claim 13, wherein the adhesive strips are made of polyvinyl chloride foam.

15. The IV guard of claim 10, wherein the cover is approximately 33.0 millimeters high, 51.0 millimeters long and at the bottom is 22.0 millimeters wide.

16. The IV guard of claim 10, wherein the adhesive strip is replaceably secured in a slot along a bottom of the sidewall.

17. The IV guard of claim 10, wherein the cover has a shape of a beaver.

18. An IV guard for use in conjunction with an intravenous connection having a cannula that is inserted into a vein of an individual through an insertion point in the individual's skin, the IV guard comprising:

a cover having an inner hollow cavity that includes a top, a front, and a pair of sidewalls that together create a shape of an animal in a substantially horizontal position, and having a head with facial features which faces the individual, a body, and a set of legs;

a back of the cover located at an end opposite the head and shaped like a tail of an animal, the back of the cover being open to allow examination of a cannula and an insertion point which are contained in the inner hollow cavity when the cover is in place over and to protect the insertion point; and a window placed along a portion of the top of the cover to allow examination of the cannula and the insertion point which are contained in the inner hollow cavity when the cover is in place over the insertion point.

19. The IV guard of claim 18, wherein the window has an oval shape and is made of a flat piece of plastic.

20. The IV guard of claim 18, wherein the cover is approximately 33.0 millimeters high, 51.0 millimeters long and an open bottom of the cover is approximately 22.2 millimeters wide.

\* \* \* \* \*